United States Patent [19]
Brigati

[11] Patent Number: 4,777,020
[45] Date of Patent: Oct. 11, 1988

[54] SHEETLIKE OBJECT SUCH AS MICROSCOPE SLIDE

[75] Inventor: David J. Brigati, Hummelstown, Pa.

[73] Assignee: Fisher Scientific Company, Pittsburgh, Pa.

[21] Appl. No.: 33,073

[22] Filed: Mar. 31, 1987

Related U.S. Application Data

[63] Continuation-in-part of Ser. No. 775,864, Sep. 13, 1985, Pat. No. 4,731,335.

[51] Int. Cl.$^4$ ............ G02B 21/34; B01L 1/00
[52] U.S. Cl. ................... 422/99; 350/354; 428/210
[58] Field of Search ........ 422/70, 100, 99, 102, 422/101; 73/864, 72; 350/534–536; 428/210

[56] References Cited

U.S. PATENT DOCUMENTS

| | | | |
|---|---|---|---|
| 2,302,830 | 11/1942 | Axelrod | 350/536 |
| 2,863,319 | 12/1958 | Melin | 73/864.72 |
| 3,358,496 | 12/1967 | Farmer | 73/864.72 |
| 4,447,140 | 5/1984 | Campbell et al. | 350/534 |
| 4,481,246 | 11/1984 | Melisz et al. | |
| 4,624,882 | 11/1986 | Melisz et al. | |
| 4,679,914 | 7/1987 | Rosenberg | |

Primary Examiner—Michael S. Marcus
Attorney, Agent, or Firm—Alan M. Doernberg

[57] ABSTRACT

A sheetlike object with a planar front face, a linear lower edge, a thickness about 0.5–5 mm and a raised pattern on a portion of the front face about 50–500 micrometers forwardly of the front face. For example, a rectangular microscope slide 25 mm wide, 75 mm high and 1 mm thick coated on one side by an adherent coating 50–500 micrometers thick. Two such slides with abutting coating portions of 50–125 micrometer thickness form a capillary gap between the remainder of the planar surfaces of 100–250 micrometer thickness. One such slide with a coating of 100–250 micrometer thickness forms a corresponding gap when placed against a flat (uncoated) slide. A similar raised portion is created by affixing a thin object (e.g., a 150 micrometer thick cover slip) to a portion of a microscope slide. Liquid is drawn into and out of the capillary gap by contacting the edge of the gap with liquids and then by absorbent.

8 Claims, 5 Drawing Sheets

SHEETLIKE OBJECT SUCH AS MICROSCOPE SLIDE

This is a continuation-in-part of U.S. Ser. No. 775,864 of Brigati, filed Sept. 13, 1985 now U.S. Pat. No. 4,731,335.

The present invention relates to sheetlike objects such as microscope slides and especially to such objects having a planar front face and a raised pattern on a portion of the front face.

Microscope slides normally have a length of either 75 mm or 3 inches (76.4 mm) a width of 25 mm or 1 inch (25.4 mm) and a thickness of approximately 1 mm. While most of the front face is generally smooth, a portion (generally on top) is often glazed in order to provide a marking surface. A product of Erie Scientific Company, SUPERFROST ® slides (described in U.S. Pat. No. 4,481,246), has a thin coating on the upper portion of the front face to form a marking surface. Such thin coating is of a substantially uniform thickness less than 30 micrometers and covers less than 20 mm of the 75 mm or 76.4 mm height.

SUMMARY OF THE INVENTION

The present invention provides a sheetlike object having a planar front face, a linear lower edge, a thickness of about 0.5 to about 5 mm and a raised pattern on a portion of the front face measuring from 50 to about 500 micrometers forwardly of the planar front face.

In many embodiments, the sheetlike object is a microscope slide and the raised pattern is either a shim, cover slip or a coating. In many such embodiments, the lower edge is one of the shorter sides (e.g., 25 mm or 25.4 mm) of the slide and the raised portion is near the top edge which is the parallel side. In such cases, the top 25–40 mm of the slide is covered by the shim, cover slip or coating.

DETAILED DESCRIPTION OF THE INVENTION

Figure 1A:
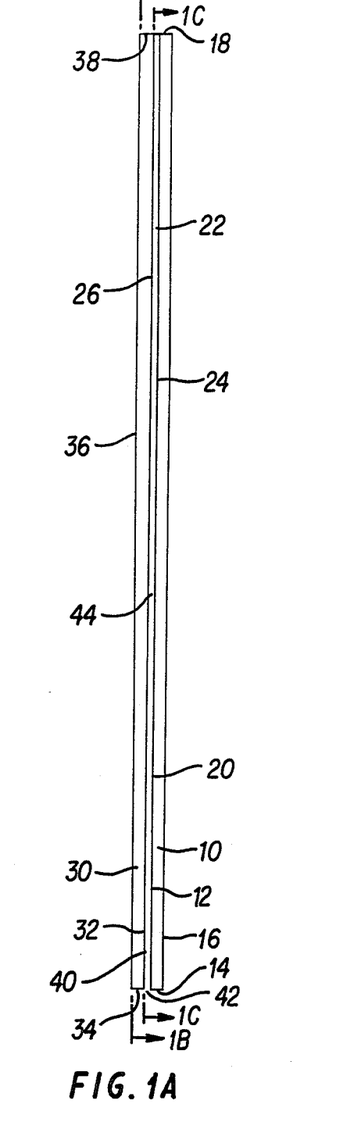
FIG. 1A is a side elevational view of a pair of microscope slides in accordance with a first embodiment of the present invention.
Figure 1B:
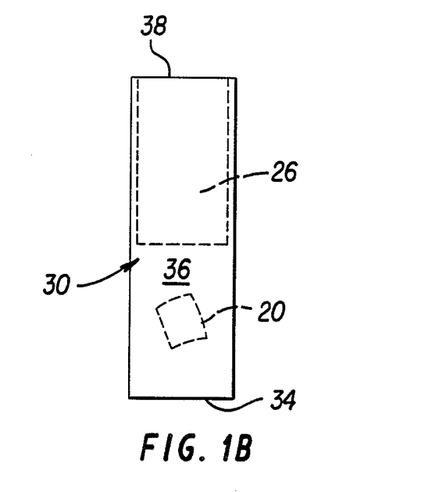
FIG. 1B is a front elevational view taken along line 1B—1B in FIG. 1A.
Figure 1C:
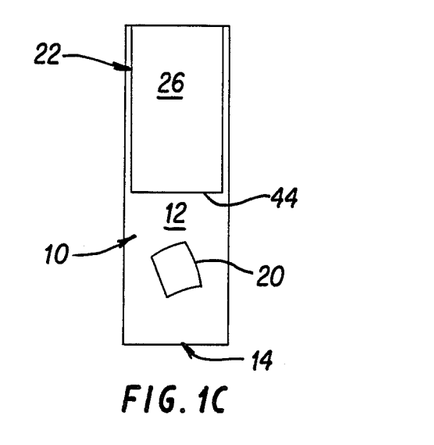
FIG. 1C is a front elevational view, in section, taken along line 1C—1C in FIG. 1A.

A first embodiment of slide pair assembly is shown in FIGS. 1A, 1B and 1C. Referring to FIG. 1A, the sample-bearing microscopic slide 10 has a sample-bearing front surface 12, a first lower edge 14, a back surface 16 and a top edge 18. A thin sample 20, such as a 5-10 micrometer thick histology specimen, is provided on a lower portion of the front surface 12. Assuming that the slide is 75 mm high, 25 mm wide and 1 mm thick (standard dimensions for a microscope slide), the sample can be a 20 mm×20 square located at least 1.0 mm (e.g., 10 mm) above the first lower edge 14.

Attached to the upper portion of the front surface 12 of the first slide 10 is a shim 22, shown in this first embodiment as two-sided adhesive tape of thickness 0.2 mm (200 micrometer). One sticky side 24 of the shim 22 adheres to the top portion of front surface 12 of first slide 10. The opposite sticky side 26 of shim 22 adheres to a facing surface 32 of facing element or slide 30. In this embodiment, facing slide 30 is also a 75 mm×25 mm×1 mm microscope slide. The shim 22 holds facing slide 30 in alignment with first slide 10 such that: facing planar face 32 of facing slide is parallel to front surface 12 and spaced therefrom by the thickness of shim 22 (200 micrometers), second lower edge 34 of facing slide 30 is coplanar with first lower edge 14 of first slide 10, back surface 36 of facing slide 30 is parallel to surfaces 32, 12 and 16 and top edge 38 of facing slide 30 is coplanar with top edge 18 of first slide 10.

The spacing of 200 micrometers is substantially constant from between the inner edges of top edges 18 and 38, along the vertical lengths of front surface 12 and facing surface 32, and to the inner edges of first and second lower edges 14 and 34. Assuming that the tape is 25 mm high (its width can be the full 25 mm width of slides 10 and 30, or can be less, e.g., 22 mm as shown), then a gap 40 is formed between the front surface 12 and the facing surface 32. This gap 40, which is 50 mm high, 25 mm wide and 0.2 mm (200 micrometers) thick, is the capillary gap terminating in lower end 42. The sample 20, being only 5-10 micrometers thick, has no significant impact upon the thickness of the gap 40, even at the height of the sample 20. Similarly, other imperfections, entrapped particles, angling of the two slides toward or away from parallel, or other factors that affect the gaps 40 by less than 20% (i.e., cause the 200 micrometer thick gap to remain between 160 and 240 micrometers in thickness) have no adverse impact, and even slightly larger variations would have no significant adverse impact. Furthermore, while the basic or average thickness of the gap in this first embodiment is 0.2 mm (200 micrometers), gaps as small as 0.05 mm (50 micrometers) or as large as 0.5 mm (500 micrometers) are permissable, with other dimensions (such as height) adjusted as described below in relation to FIG. 4. Under appropriate circumstances, thickness of the gap still less than 50 micrometers or more than 500 micrometers may also be appropriate. As described below, however, the preferred thickness of the gap is 150–250 micrometers, more preferably 150–200 micrometers.

FIG. 1B shows the same slide pair assembly from the front. The facing slide 30, with its back surface 36 on front, completely covers the first slide 10, from the top edge 38 to the bottom edge 34 of the facing 30. Sticky side 26 of shim 22 can be seen under the top portion of facing slide 30; and sample 20, which is immobilized on sample slide 10, can be seen centered under the lower portion of facing slide 30. The precise vertical alignment shown in FIG. 1B, wherein neither side of first slide 10 extends beyond the corresponding side of facing slide 30, is not critical. Misalignment in such direction of 2 mm, or even 5 mm, is of no significant adverse impact. Furthermore, as indicated above, the widths need not all be equal (e.g., 25 mm).

FIG. 1C shows the same front view as FIG. 1B, but now in section so as to look behind facing slide 30. The front face 26 of shim 22 occupies the top 25 mm of the visible surface. The bottom 50 mm×25 mm of front surface 12 of first slide 10 (below lower end 44 of shim 22) is now visible; it is this 50 mm×25 mm that is exposed to the capillary gap 40. The sample 20 occupies a 10×10 mm portion centrally located within this 50 mm×25 mm portion of sample-bearing surface 12. The height of the gap can be adjusted by using shorter or longer pieces of tape as shim: e.g., 25 mm wide and 20, 30, 40 or 50 mm long (high) tape.

Figure 2A:
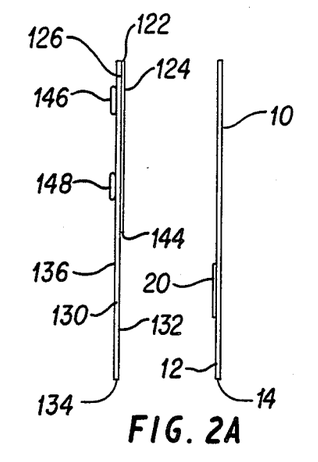
FIG. 2A is a side elevational view of a disassembled slide pair according to a second embodiment of the present invention.
Figure 2B:
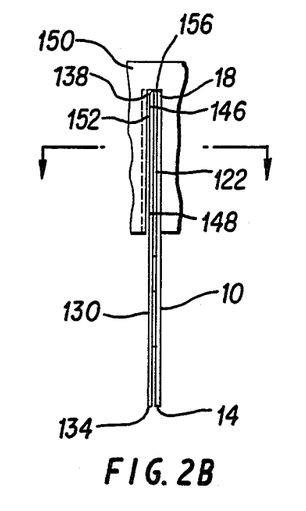
FIG. 2B is a view similar to FIG. 2A of the same slide pair assembled within a holder portion into a slide assembly.
Figure 2C:
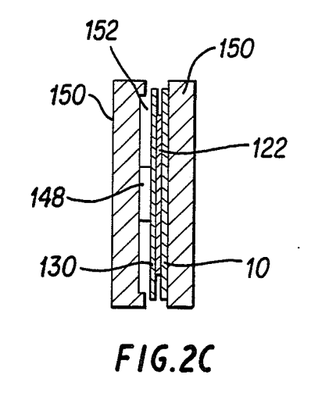
FIG. 2C is a top view of the slide assembly in a holder taken in section along line 2C—2C in FIG. 2B.

FIGS. 2A, 2B and 2C illustrate a second embodiment of slide pair assembly. First slide 10 with first lower edge 14, front surface 12 and sample 20 thereon is identical to corresponding elements in FIG. 1A. The facing slide 130 is also a 75 mm×25 mm×1 mm microscope slide, with facing surface 132 and second lower edge 134, but now the shim 122 is a 40 mm×25 mm (or 22 mm)×0.15 mm glass cover slip having a lower end 144. The first 40 mm×25 mm surface 124 of shim 122 faces (and, when assembled in FIG. 2B abuts against) the upper portion of front surface 12 of first slide 10. The second 40 mm×25 mm surface 126 of shim 122 is glued to the upper portion of facing surface 132 of facing slide 130.

Along the back surface 136 of facing slide 130 are provided upper and lower elastomeric protuberances 146 and 148, shaped as O-rings, compressible flat springs or rollers or solid discs, which may have beveled upper portions (not shown).

In FIG. 2B, the slide of FIG. 2A is assembled by placing slides 10 and 130 together in parallel and slipping their upper ends into a recess of dimensions 30 mm high, 26 mm wide and 2.4 mm thick formed in holder 150. The recess opens downwardly and has, on its top, a horizontally-extending aligning face 156. Top edges 18 and 138 of first slide 10 and facing element 130 about against aligning face 156. Protuberances 146 and 148 are engaged within a vertically extending, downwardly opening slot 152 within the back wall of the recess formed in holder 150, so as to force the upper portion of facing element 130 and all of shim 122 against the upper portion of first slide 10. This combination of engagement means causes the first slide 10 and facing slide 130 to be aligned in parallel, with a gap the thickness of shim 122 (0.15 mm), the width of slides 10 and 130 (25 mm) and the height (35 mm) not covered by shim 122. Lower edges 14 and 134 are at the same height and are spaced from each other by substantially the same distance as the thickness of shim 122, i.e., 0.15 mm.

FIG. 2C is a top view of FIG. 2B taken along line 2C—2C in FIG. 2B. In this sectional view, protuberance 148 is seen inside its slot 152 which is cut into the slide holder 150 as a downwardly open slot in the recess. Protuberance 148 presses against slot 152 and compresses shim 122 which is glued to the opposite side of facing element 130. This in turn exerts pressure on the upper portion of the first slide 10 which is held in place by holder 150. In this manner the upper portion of the facing slide 130 and the first slide 10 are kept in contact and suspended vertically below. Since slot 152 is downwardly open, the facing slide 130 and the first slide 10 may be easily inserted into and removed from the recess in the holder 150 by the guiding action of slot 152 on protuberances 146 and 148.

Figure 2D:
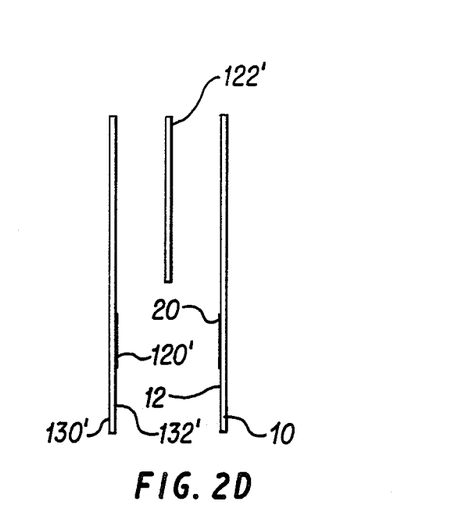
FIG. 2D is a view similar to FIG. 2A of a disassembled slide assembly according to a third embodiment of the invention.
Figure 2E:
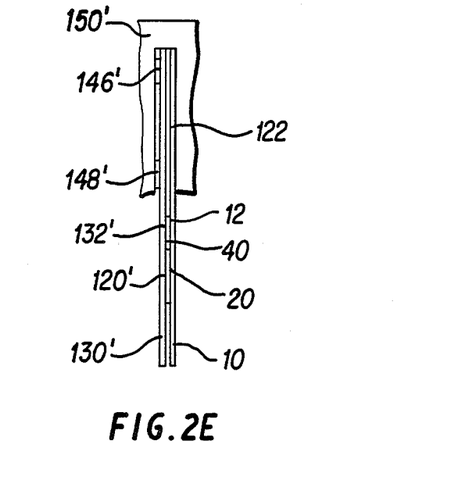
FIG. 2E is a view similar to FIG. 2B of the slide assembly of FIG. 2D in a holder.

FIGS. 2D and 2E illustrate a third embodiment differing from that of FIG. 2A in that the protuberances 146' and 148' are now located on the interior of the recess within the holder 150' rather than on the back surface 136 of facing element 130.

Referring to FIG. 2D, the sample-bearing microscope slide 10 has its sample bearing front surface 12 facing a second sample bearing microscope slide 130' and its sample-bearing 132'. Thin sample 20 on sample bearing microscope slide 10 is present opposite sample 120' on the opposite sample-bearing slide 130'.

Referring to FIG. 2E, sample-bearing slides 10 and 130' are held in place in the recess in holder 150' by the pressure of the elastomeric protuberances 146' and 148' pressing against their upper portions. Shim 122' is sandwiched in between their upper portions. Sample 120' immobilized on sample bearing surface 132' of the second sample bearing slide 130' is held in the gap 40 produced by the close apposition of the sample-bearing surfaces held in place across and on the opposite side of the gap 40 from sample 20 by the pressure of protuberances 146' and 148' and the holder 150' on the upper portions of the two sample bearing slides 10 and 130' against shim 122'.

A plurality of such slide pairs can be held in a parallel array as described in relation to FIGS. 3A and 5 in U.S. Ser. No. 775,864. Furthermore, such an array of slide pairs can be lowered onto an array of droplets of treating liquid as described in relation to FIGS. 3B and 7 of U.S. Ser. No. 775,864. Finally, such a step can be part of a multi-step process of treating samples on the slides with a series of treating liquids, some of which are provided on droplet holders and others as sheets or baths of liquid as described in relation to FIG. 6 of U.S. Ser. No. 775,864. Such descriptions are incorporated herein by reference.

Figure 3A:
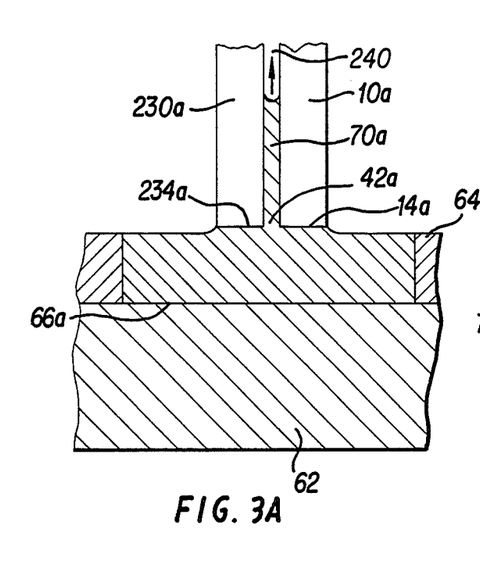
FIG. 3A is a magnified side elevational view of the bottom of the slide assembly of FIG. 2B or 2E contacting a droplet of treating liquid, showing liquid being drawn vertically into the thin gap by capillary flow.

FIG. 3A hereof (corresponding to FIG. 3C of U.S. Ser. No. 775,864) shows liquid being drawn by capillary action from a hole 66a through an elastomeric member 64 on a rigid base 62. Prior to contact by the slide pair, liquid stood up in hole 66a above the top surface of elastomeric member 64. Upon lowering the slide pair consisting of slide 10a (corresponding to slide 10 in FIGS. 2B or 2E) and slide 230a (corresponding to slide 130 in FIG. 2B or slide 130' in FIG. 2E), the gap 42a between lower edges 14a and 234a contacts the droplet. A capillary column of liquid 70a rises in capillary gap 240 between slides 10a and 230a by capillary action. This effect is enhanced by the relative incompatibility of the liquid with the surface of elastomeric member 64, e.g., because the aqueous droplet is repelled by the hydrophobic surface of elastomeric member 64. Such incompatibility (evidenced by beading of the treatment liquid if it were placed on a flat surface of elastomeric material used for member 64) also causes the droplets to stand above the top surface of member 64.

Figure 3B:
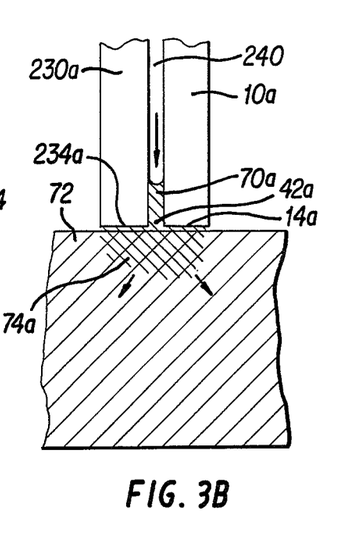
FIG. 3B is a view, similar to FIG. 3A, of liquid being drawn vertically out of the thin gap by capillary flow into an absorbent material.

After the capillary column 70a has risen as far as capillary action will take it (typically about 30 to 40 mm in the indicated gap of 0.15 mm), the slide assembly can be lifted by its holder away from elastomeric member 64. Each slide pair (e.g., 10a/230a) will hold, by capillary action, the treating liquid received from one or more droplets with which its lower space (e.g., 42a) has been contacted. After the liquid has remained in the gap for a desired time period, the slide assembly is now lowered onto an absorbent material 72 as shown in FIG. 3B. Since the liquid is more compatible with the absorbent material 72 than with the surfaces of slides 10a and 230a, now the capillary column 70a will descend, with the treating liquid spreading downward and outwardly as a liquid front 74a within absorbent material 72. Within a matter of seconds, the gap 240 between the slide pair will be evacuated essentially completely of liquid by such capillary action, except perhaps for minute amounts that may adhere to the sample or to other hygroscopic surfaces along the slide gap 240 or lower edges 14a and 234a. Once the liquid is evacuated from the slide gap 240, the slide pair may now be moved to another droplet holder, or to a sheet or bath of treating liquid for the next step of a multi-step treating process such as is described in U.S. Ser. No. 775,864. FIG. 3B hereof corresponds to FIG. 3D of U.S. Ser. No. 775,864.

Figure 4:
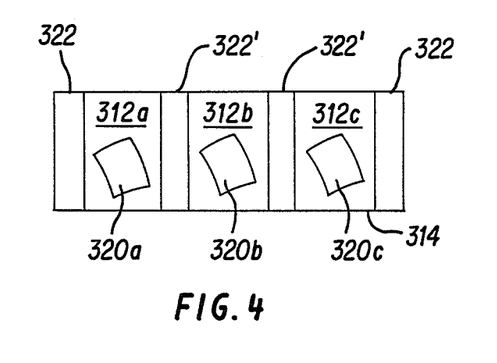
FIG. 4 is a front elevational view in section, similar to that of FIG. 1C, of a slide assembly according to a fourth embodiment of the present invention.

FIG. 4 illustrates, in a view similar to that of FIG. 1C, an embodiment of the invention wherein three vertically-extending sample-bearing surfaces are formed on one 75 mm×25 mm slide. The slide extends horizontally with its 75 mm lower edge 314. Two outer shims 322 of 25 mm height, 2 mm width and 0.25 mm thickness extend vertically on the front (75 mm×25 mm) face. Two inner shims 322' have similar 25 mm×2 mm×0.25 mm dimensions, and are equally spaced from and parallel to end shims 322. Such shims 322 and 322' can be formed by applying a thermosetting material (e.g., epoxy or silicone or paint) to the face of a glass slide. The uncovered and isolated faces are therefore 312a, 312b and 312c, each extending upwardly 25 mm from lower edge 314, and each approximately 22.33 mm in width. A facing slide can be placed over this first slide, so that gaps of 0.25 mm thickness, 25 mm height and 22.33 mm width will form over faces 312a, 312b and 312c. By contacting the lower space of each such face which is adjacent to lower edge 314 by a treating liquid and then by an absorbent material, liquid reagent can be drawn into and out of each gap as described above. Such a slide pair can be applied to droplets or to a bath or sheet of treating liquid manually.

Although shims 322 and 322' of FIG. 4 are indicated as being 0.25 mm (250 micrometers) thickness, a thinner coating (e.g., 150 or 200 micrometers) can be used even with a flat glass slide forming the other half of the slide pair. It is also suitable, however, to employ pairs of slides each with coatings for shims 322 and 322' of lesser thickness (e.g., 50, 75, 100 or 125 micrometers) which will press against each other in the slide pair so as to have a spacing between glass surfaces of 100, 150, 200 or 250 micrometers, respectively. It is also suitable, in such cases, to have other regions of the slide (e.g., portions of the top 20% of each of faces 312a, 312b and 312c) covered with a coating of similar thickness.

Alternatively, a series of such horizontally-extending slide pairs, each with three vertically-extending capillary gaps, can be held within a holder using, for example, the slide rack shown in FIG. 1 of U.S. Pat. No. 4,199,613 of Johnson, with such modification as is required to leave lower edges 314 of each sample-bearing slide available for contact by droplets or sheets of treating liquid. The "shims" of Johnson in this embodiment would not necessarily be attached to the slide rack, nor would they be positioned between a sample slide and its companion facing slide to help form the capillary gap between them, but would rather be located at both lateral ends and pressing on the outer surface of the facing and sample bearing slides, forcing them together by compressing the facing slide and the sample bearing slide against shims 322 described above. In this embodiment, shims 322 and 322' in FIG. 4 would be the only parts defining the first distance of the capillary gap between the facing and sample bearing slide.

The thickness of the side walls of the recess in the holder would then define a second distance separating parallel pairs of facing and sample bearing slides. This second distance is not designed for capillary action and separates sets of slide pairs so that liquid reagents can be drawn up into them through the capillary gap from discrete droplets as in FIGS. 3A and 3B. This second distance can be any thickness greater than 1 mm, which is significantly thicker than the 200 microns of Johnson's shims or the shims described in this patent. The preferable length of this second distance and, therefore, the preferable thickness of the side walls forming the borders of any downwardly open slide recess in the slide holder, ranges from 5-7 mm. Using this range, the greatest number of slides can be engaged into a slide holder for the purpose of drawing up, incubating and removing liquid reagents from the capillary gaps between adjacent slide pairs.

This second distance range allows adjacent capillary gaps to be maintained from 7-9 mm apart. At this distance, individual droplets in the droplet holder can be maintained apart without contaminating each other by inadvertently overcoming the incompatibility of the surface of elastomeric member 64 and the individual droplets in the droplet holder. Such advantage would not be possible with the slide rack of Johnson where 200 microns is too close to stably separate adjacent reagent droplets on the hydrophobic droplet holder. Therefore, the slide rack of Johnson would have to be completely and substantively modified from its original description to achieve the advantages of the present invention.

To cause the liquid to rise 15-20 mm above lower edge 314, the gap (thickness of shims 322 and 322') may be thicker than the 0.15-0.20 mm thickness most preferred in the earlier embodiments, where liquid was intended to rise 25-45 mm above lower edge 14. Through routine experimentation, the gap can be adjusted (by varying shim thickness) to achieve the desired vertical rise of liquid for any sample-bearing slide surface.

Figure 5A:
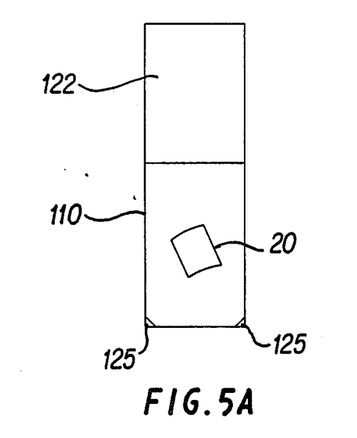
FIG. 5A is a front elevational view of a partially-coated slide according to a fifth embodiment of the present invention.
Figure 5B:
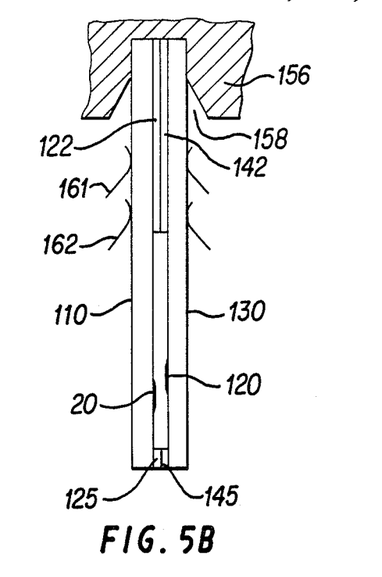
FIG. 5B is a side elevational view of two of the slides shown in FIG. 5A inserted together into a holder of a different design, similar in view to FIGS. 2B and 2E.

FIGS. 5A and 5B show an embodiment of the invention wherein a pair of slides 110 and 130 are held in a holder which is described in more detail in an application of Brigati and Cuomo U.S. Ser. No. 032,874, filed Mar. 31, 1987 and commonly-assigned, which is also a continuation-in-part of U.S. Ser. No. 775,864.

In FIG. 5A, one of the slides 110 is shown. A top coating 122 covers the top portion of the slide (e.g., the top 31.8 mm out of a total height of 76.2 mm). Small triangular coating portions 125 cover the bottom left and right corners of slide 110. Each of these coatings are one-half the thickness of the desired gap (e.g., each 80 micrometers thick to form a 160 micrometer thick gap). A sample 20 of tissue is placed on slide 110 below coating 122.

FIG. 5B is a side view of two identical slides 110 and 130 in a slide holder. Top coating 122 abuts against identical top coating 142 on slide 130. Bottom corner coating 125 abuts against bottom corner coating 145 in slide 130. Slides 110 and 130 are pressed together by clips 161 and 162 which are, respectively, above and below the midpoint of coatings 122 and 142. The tops of slides 110 and 130 are received within a slot 158 of alignment strip 156 of the slide holder. The horizontally-extending surface of the slot 158 maintains precise vertical alignment between slides 110 and 130. For the holder described in U.S. application Ser. No. 032,874, slots are provided near each two top corners of slides 110 and 130 and side walls are provided to maintain horizontal alignment between slides 110 and 130 in a direction into the page in the view of FIG. 5B. In such slide holder, each alignment strip has multiple slots (illustrated as ten) so that multiple (ten) slide pairs can be held in a fixed array.

As shown in FIG. 5A, two lower corners of slide 110 (slide 130 is similar) are coated with an 80 micrometer thick coating which is triangular in shape, so as to extend 4 mm up and 4 mm in from each corner along the side and bottom edges of the first slide 110. The triangular coating on first slide 110 is labeled 125; the triangular coating on second slide 130 is labeled 145. Accordingly, the 160 micrometer thick gap is maintained, but flares out at a 45 degree angle from a width of 17.4 mm at the lower edge to a width of 25.4 mm at a height of 4 mm above such lower edge.

In use, up to thirty slide pairs (with samples on one or both slide of each pair) are inserted into the holder. The holder is then lowered onto a series of liquids, typically liquid reagents. Each liquid may be in the form of a bath or sheet, in the form of individual round droplets supported on a droplet holder (see FIG. 7 of U.S. Ser. No. 775,884) or in the form of laterally-extending aliquots on a modified droplet holder (see FIGS. 3A, 3B and 3C of an application of Brigati, U.S. Ser. No. 032,875, filed Mar. 31, 1987, commonly-assigned and also a continuation-in-part of U.S. Ser. No. 775,884). Liquid rises by capillary action into the gap between each first slide 110 and the adjacent second or facing slide 130. See FIG. 3A hereof. After the appropriate time of liquid contacting sample on one or both slides, the slide assembly is then lowered on a flat blotter. Liquid is then drawn by capillary action into the blotter so as to evacuate each capillary gap, as shown in FIG. 3B hereof. If a droplet holder is used for the particular step, then the process can be individualized so as to treat different slide pairs with different liquids (e.g., different primary antibodies, nucleic acid probes, enzymes or chromogens). After evacuation, the slide assembly can then be contacted by another reagent in the form of droplets, laterally-extending aliquots or a sheet or bath of liquid.

Figure 6A:
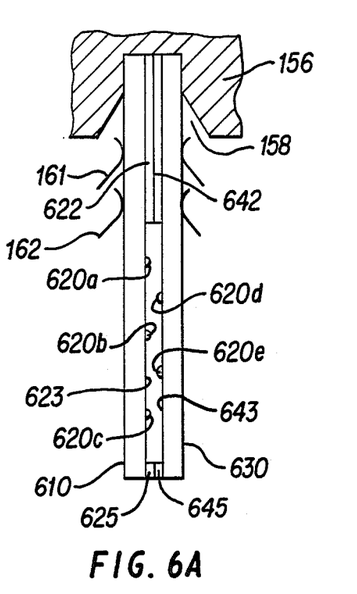
FIG. 6A is a side elevational view similar to FIG. 5B, of two slides according to a sixth embodiment of the present invention inserted together into the same slide holder as is shown in FIG. 5B.

FIG. 6A is a view similar to FIG. 5B, but enlarged, of two slides 610 and 630 adapted for either a dotting or a blotting assay. In blotting (unlike dotting), the sample is subjected to a geometric separation before transfer to the filter material. Slides 610 and 630 are fitted into the same slide holder. Upper coatings 622 on slide 610 and 642 on slide 630 abut against each other under the compression of clips 161 and 162. Slides 610 and 630 fit at their upper ends into slot 158 in alignment strip 156 of the holder. A thin strip of nitrocellulose material or other membrane filter material 623 covers the inner surface of slide 610 below coating 622. A thin strip of nitrocellulose or other filter material 643 covers the inner surface of slide 630 below coating 642. Slides 610 and 630 need not be glass, and preferably are of a thermoplastic or thermosettig material to which thin strips 623 and 643, respectively, can tightly bind.

The gap between facing surfaces of thin strips 623 and 643 has the thickness of the first distance of U.S. Ser. No. 775,864 (generally 50 to 500 micrometers, preferably 150 to 250 micrometers, more preferably 150 to 200 micrometers). If each of thin strips 623 and 643 is 50 micrometers thick, then a gap of 150 micrometers can be created by making each of coatings 622 and 642 a thickness of 125 micrometers. Furthermore, slide 610 can be formed (especially if plastic) as a unitary structure with a top portion extending 125 micrometers further forward than the bottom portion either by molding, by removing material from the lower portion or otherwise. Thin strip 623 can be attached chemically, with adhesive or by heat setting (analogous to ironing on) if slide 610 is of an appropriate material. The entire structure represented by slide 610, coating 622 and layer 623 can also be formed as a laminant, by analogy to FIGS. 17-20 of U.S. Pat. No. 4,308,028 to Elkins.

In use in a dotting assay, slide 610 is spotted directly with samples (such as cells or cellular extracts of protein or DNA) using a manual or automatic pipetting device. The samples are bound to the membrane of filter material on slide 610 by heating, drying or chemical linkage. The thin strips of slides 610 and 630 are then apposed, and their upper ends are placed in slot 158 in alignment strip 156 of the holder to form the capillary action gap depicted in FIGS. 6A and 6B.

In use for blotting, slide 610 (and separately slide 630) is blotted against an electrophoretic gel or other separating device so as to transfer previously separated species (e.g., antigens or polynucleotides) onto strip 623 in a defined spatial relationship (e.g., short polynucleotides migrate further into a gel than longer ones). The slide is then removed from the gel or vice versa. The blotted material can then be more firmly attached to the nitrocellulose by drying or heating or by using chemically linking reagents (e.g., glutaraldehyde) if desired. In FIG. 6A, three specimen spots 620a, 620b and 620c are shown on nitrocellulose strip 623. Three other specimen spots 620d and 620e are shown on nitrocellulose strip 643. These specimen spots, irrespective of whether they were spotted or blotted onto the membrane, can then be exposed to a series of probing, analyzing, washing, treating and developing reagents in a manner analogous to the multi-step process described for tissue specimens in U.S. Ser. No. 775,864. At the conclusion of the process, a chromphore would be deposited at the locus of each spot for which the reagents are specific. Thus, for example, a restriction enzyme digest of a DNA source can be electrophoresed, blotted and probed to see what lengths of restriction fragments have the sequence probed for.

Figure 6B:
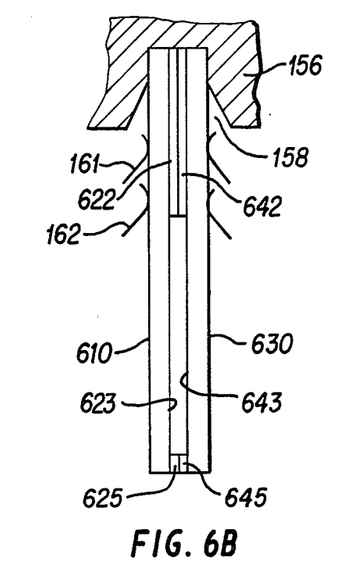
FIG. 6B is a side elevational view, similar to FIGS. 5B and 6A, of two slides according to a seventh embodiment of the present invention inserted together into the same slide holder as is shown in FIGS. 5B and 6A.

FIG. 6B shows a corresponding slide pair on which the nitrocellulose strips 623 and 643 have reactive groups (such as carboxy or amino) which can be spotted with binding pair members (e.g., antigens, antibody or nucleic acid sequences). Chemical attachment of such binding pair members can be performed in advance by conventional linking chemistry (e.g., carbodiimide chemistry). Alternatively, loci on the membrane can be spotted to have defined pre-bound chemically reactive groups (e.g., N-hydroxysuccinimide, azido, or aldehyde groups) which directly bind to reactive moieties of sample materials (e.g., amino, carboxy, sulfhydryl, purine, pyrimidine or hydroxyl groups) when the sample comes in contact with the loci in the course of filling the capillary action gap with sample. In these cases (unlike those described previously), the slide assembly of slides 610 and 630 is formed without a sample pre-bound on either slide. Either as the initial step or after one or more preparative washing steps (by capillary drawing and evacuation as in FIGS. 3A and 3B), a sample material such as a drop of serum is drawn up into the gap between strips 623 and 643 by capillary action (in a fashion analogous to that shown in FIG. 3A). The assembly is then incubated at an appropriate temperature or temperature profile. If binding occurs, then analyte material in the sample would bind at the appropriate loci of strip 623 or 643. For example, if a viral antigen is bound at one locus on nitrocellulose strip 623, any antibody to that antigen in the serum sample would bind at that locus. Other antibodies in the serum sample would not. The gap could then be evacuated and subjected to various washing steps corresponding to steps 18A–19B of the staining procedure on pages 23–29 of U.S. Ser. No. 775,864. Next, a labeled antibody could be brought in which is specific for any human antibody (e.g., rabbit anti-human Ig) or is specific for certain human antibodies (e.g., goat anti-human IgG). The label can be directly readable (e.g., a fluorescent tag), a site for further attachment of readable label (e.g., biotin serving as a site for avidin-enzyme, avidin-fluor or ABC reagents) or an enzyme (e.g., horseradish peroxidase or alkaline phosphatase). If enzyme is then present where serum antibody had originally bound, then (after further washing) chromogen can be brought in (by analogy to steps 23A to 25B of such staining procedure). At the conclusion of such process, slide 610 can be examined by the naked eye, by a microscope or by an electronic visualization device to determine if color is present at that spot as an indication if (and semiquantitatively how much of) the looked for antibody was present in the serum sample.

The advantage of this strategy is that the loci can be compared to the surrounding membrane as a control, or to other spots to provide a simple reference system for quantitation. For example, such other spots could have pre-bound known amounts of analyte, in either a single or multiple amounts. Alternatively, another spot could have pre-bound negative controls, or a pre-bound binding partner for a binding pair member with which the sample is spiked to serve as a calibrator or internal control for the read-out.

It should be appreciated that a single sample can be simultaneously assayed for antibodies against different antigens, if these antigens are pre-bound as spots in a known pattern on strips 623 and 643. Alternatively, identical spots can be formed on strips 623 and 643 to be exposed to the same serum sample and washed. The slides can then be removed from the holder and rearranged in different slide pairs so that, for example, slide 623 is exposed to anti-human Ig antibody and then developing reagents while slide 643 is exposed to anti-human IgG antibody and then developing reagents. In a third format, a single sample can be analyzed for many antigens if antibodies to these antigens are pre-bound as spots in a known pattern on strips 623 and 643. In a fourth format, specific nucleic acid sequences are spotted at defined loci on the strips 623 and 643 for hybridization assays with prepared samples, such as those wherein sample nucleic acid has been exposed, labeled and placed in suitable hybridization media for denaturation and hybridization. Such fourth format can also be used for nucleic acid sandwich assays.

The present invention thus provides in some forms an array of slide pairs, each extending vertically and terminating at lower edges in a common horizontal plane. The surface of each slide which is designed to bear a sample (either or both of each slide pair) is separated from a facing surface of the other slide of the slide pair by a first distance which is sufficiently small to promote capillary action, as described below. Such first distance is typically about 50–500 micrometers and more preferably about 150–200 micrometers. As indicated in U.S. Ser. No. 775,864, each of the two facing surfaces may bear one or more samples, or sample may be present on only one surface.

In the present array, adjacent pairs of slide pairs are separated by a second distance sufficiently large for the adjacent capillary gaps to be separated by about 7–9 mm or more. Thus, if the slides are each 1 mm thick, a second distance of 5–7 mm will yield a 7–9 mm spacing between capillary gaps (see FIG. 3A of U.S. Ser. No. 775,864).

The first distance can be established by various shims or materials between or on the facing slides. Thus, as illustrated in FIG. 1A, a two-sided adhesive tape of 200 micrometer thickness between the upper portions of facing slides will establish a 200 micrometer thick gap between the middle and lower portions of the two slides. Alternatively, as illustrated in FIG. 2A, a 0.15 mm (150 micrometer) thick cover slip fastened to the top portion of one of the two slides will establish a 150 micrometer thick gap between the middle and lower portions of the two slides. Alternatively, as illustrated in FIG. 2D, the cover slip can be sandwiched between the top portions of the two slides without being affixed to either. Finally, the gap distance can be established by building up a portion of the surface on one of the two slides, as illustrated by FIG. 4. There, four shims of 250 micrometer thickness are formed on a microscope slide by applying a thermosetting material (e.g., epoxy or silicone or paint). A similar effect could be achieved by building up facing surfaces of both slides (e.g., 125 micrometer thick polymeric coatings on each). A preferred range for built-up areas on both facing slides is 50–150 micrometers, especially 75–100 micrometers.

In considering each slide alone, a coating, preferably on the top portion of one surface, extends above the plane of the glass surface by about 50 to about 500 micrometers. This relatively broad range encompasses slides to be matched with flat slides, in which case the built up surface is preferably about 100–500 micrometers and more preferably 150–250 micrometers. The broad range also encompasses slides to be matched with similarly modified slides, in which case the built up surface is preferably about 50–250 micrometers, more preferably 75–125 micrometers.

The second distance can also be established in a variety of ways. As illustrated in FIGS. 3A and 5 of U.S. Ser. No. 775,864, each pair of slides can be fitted (with a shim or the like between them in many cases) into a slot in a holder. Each slot in the holder can then be separated from the next slot by the second distance. Alternatively, as illustrated by the description at page 16, line 32 through page 18, line 5 of U.S. Ser. No. 775,864, a relatively thick shim (e.g., 5–7 mm thick) can separate each slide pair from the next slide pair. Such an array can be used whether the vertically extending face of each slide is the longest dimension of the slide (as in the 75 mm height of FIG. 1A) or is a shorter dimension of the slide (as in the 40 mm height of FIG. 4).

The present invention further includes modified microscope slides adapted to form such slide arrays. For modified slides to be used in a slide pair with a flat slide, a portion should be built up (e.g., by affixing a cover slip or coating with polymer) to the full thickness of the desired gap (e.g., 50–500 micrometers, typically 150–200 micrometers). For modified slides to be used with other modified slides, a lesser thickness is permissable, e.g., 25–250 micrometers, typically 75–100 micrometers. Thus, in one preferred pattern, two facing slides with matching built up areas of 100 micrometer thickness will form a 200 micrometer thick capillary gap.

The built up areas of one or both slides can cover most or all of the width of the slide from the top end partially downward (e.g., the top 25–40 millimeter of a 75 mm long slide). FIGS. 1A, 1B, 1C and 2A illustrate such a pattern. Alternatively, the built up areas may be otherwise arranged on the slide surface, such as in FIG. 4, where two outer shims of 25 mm height, 2 mm width and 0.25 mm thickness cover the sides of a surface. Two inner shims of identical size in that embodiment also separate the slide pair and have the further effect of dividing the slide surface into three isolated faces 25 mm high and approximately 22 mm in width.

The built up areas of the present modified slides differ from conventional frosted slides wherein the modified portion is in or slightly behind the plane of the unmodified portion (because the frosting process removes rather than adds material). Products are also commercially available from Erie Scientific Company under the "SUPERFROST" and "COLORFROST" trademarks wherein a white, opaque coating is placed on the top portion (e.g., the top 15 mm out of 75 mm) of a slide surface. Such coating is designed to establish a writing surface and not to create a gap, and is furthermore typically no greater than 20 micrometers in thickness. Thus, U.S. Pat. No. 4,481,246 speaks of typical thickness of coating being 0.0003 to 0.0008 inch, corresponding to 7–18 micrometers. Even if one were to form a gap with two such SUPERFROST slides facing each other (a combination not disclosed in the art), the gap thickness of 40 microns or less would be undesirably small relative to the 5–10 micrometer thickness of many samples and the up to 50 micrometer thickness of some samples that one may expect to encounter. With the gap so close in thickness to the sample thickness, drainage of trapped liquids with significant surface tension such as water, buffers and other commonly-encountered liquids and especially aqueous liquids becomes impossible or at least incomplete. Such trapped liquids cause contamination of subsequently applied reagents or even prevent the entrance of the next reagent in the sequence. Therefore, variability in results might be expected of identical treatments of samples of thicknesses which differ. Such difficulties are avoided in the present invention by using thicker coatings, at least 50 micrometers in thickness, to yield capillary gaps of adequate width for filling and evacuating.

What is claimed is:

1. A sheetlike object consisting essentially of a substrate having a planar front face, a plurality of edges including a linear lower edge, a thickness of about 0.5 to about 5 mm and a raised pattern coated on a substantial width portion of the front face, the raised pattern extending about 50 to about 500 micrometers forwardly of the planar front face.

2. The sheetlike object of claim 1 being a microscope slide with a planar front face, the linear lower edge being a side of the microscope slide.

3. The sheetlike object of claim 2 wherein the microscope slide has two parallel long sides and two parallel short sides and wherein the linear lower edge is one of the two long edges.

4. The sheetlike object of claim 2 wherein the microscope slide has two parallel long sides and two parallel short sides, where the linear lower edge is one of the two parallel short sides, and wherein the raised portion is primarily adjacent to the other of the two parallel short sides, which is the top edge.

5. The sheetlike object of claim 4 wherein the raised portion covers the microscope slide from the top edge to a line from 33% to 60% of the distance from the top edge to the bottom edge.

6. The sheetlike object of claim 5 wherein the raised portion is of a substantially uniform thickness which is about 100 to about 250 micrometers.

7. The sheetlike object of claim 5 wherein the raised portion is of a substantially uniform thickness which is about 50 to about 125 micrometers.

8. The sheetlike object of claim 7 wherein the substantially uniform thickness is about 75 to about 100 micrometers.

* * * * *